(12) United States Patent
Wei

(10) Patent No.: US 6,743,801 B2
(45) Date of Patent: Jun. 1, 2004

(54) 1,2,3,6-TETRAHYDROPYRIMIDINE-2-ONE COMPOSITIONS AND THERAPEUTIC METHODS THEREWITH FOR PAIN AND INFLAMMATION

(76) Inventor: Edward T. Wei, 480 Grizzly Peak Blvd., Berkeley, CA (US) 94708

( * ) Notice: Subject to any disclaimer, the term of this patent is extended or adjusted under 35 U.S.C. 154(b) by 0 days.

(21) Appl. No.: 10/232,798

(22) Filed: Aug. 29, 2002

(65) Prior Publication Data

US 2003/0207904 A1 Nov. 6, 2003

Related U.S. Application Data

(63) Continuation-in-part of application No. 10/139,193, filed on May 2, 2002.
(51) Int. Cl.[7] ........................ A61K 31/513; A61K 38/18
(52) U.S. Cl. ........................ 514/269; 514/345; 544/318
(58) Field of Search ................................. 514/269, 345; 544/318

(56) References Cited

U.S. PATENT DOCUMENTS

| | | | |
|---|---|---|---|
| 3,821,221 A | 6/1974 | Podesva et al. ............. | 260/251 |
| 5,116,868 A | 5/1992 | Chen et al. .................. | 514/546 |
| 5,192,802 A | 3/1993 | Rencher ...................... | 514/535 |
| 5,800,485 A | 9/1998 | Trop et al. ................... | 607/105 |
| 5,942,545 A | 8/1999 | Samour et al. .............. | 514/573 |
| 6,166,044 A | 12/2000 | Sandborn et al. ........... | 514/343 |
| 6,319,513 B1 | 11/2001 | Dobrozsi ..................... | 424/434 |
| 6,365,190 B1 | 4/2002 | Gordon et al. .............. | 424/489 |
| 6,391,869 B1 | 5/2002 | Parks et al. ............. | 514/211.07 |

OTHER PUBLICATIONS

Babes, et al, Cooling inhibits capsaicin . . . Neuroscience Letters 317: 131–134; 2002.
Barnes P.J. Neurogenic inflammation in the airways. Respiratory Physiology 125: 145–154, 2001.
Handwerker, et al., Discharge patterns of human C–fibers induced by itching and burning stimuli. J. Neurophysiol. 66: 307–315, 1991.
McKemy et al., Identification of a cold receptor reveals a general role for TRP channels in thermosensation. Nature 416: 52–58, 2002.
Nair, B., Final report on the safety assessment of Mentha Piperita (Peppermint) Oil, . . . Int. J. Toxicol. 20 Suppl 3: 61–73, 2001.
Watson, H. R., R. Hems, D.G. Roswell & D. J. Spring, New compounds with the menthol cooling effect, J. Society Cosmetic Chemists. 29, 185–200 (1978).
Wei, E.T. Chemical stimulants of shaking behavior. Journal Pharmacy and Pharmacology 28: 722–724, 1976.
Wei, E.T. Pharmacological aspects of shaking behavior produced by AG–3–5, TRH, and morphine withdrawal. Federation Proceedings 40: 1491–1496, 1981.
Wei, E.T. and D.A. Seid. AG–3–5: A chemical producing sensations of cold. Journal Pharmacy and Pharmacology 35: 110–112, 1983.
Gray et al (Perineal Skin Care . . . ), Woundcare 15: 170–177, 2002.
Reuse (Comparisons of various histamine . . . ), British Journal of Pharm., vol. 3, pp. 174–180, 1948.
Sciarra and Sicarra, Chpt. 50, "Aerosols" in "Remington, the science and practice of pharmacy", 20th ed. Lippincott Williams & Wilkins, 2000.
School of Pharmacy, U. of North Carolina, Internet site (www.pharmlabs.unc.edu or www.Unc.edu/courses/phar051/ointments): Ointments: prep and evaluation of Drug release, Jun. 30, 2002.
Block, Chpt. 44, Mediated Topicals, pp. 836–857, in "Remington, the science and practice of pharmacy", 20th ed. Lippincott Williams $ Wilkins, 2000.

*Primary Examiner*—Richard L. Raymond
*Assistant Examiner*—Tamthom N. Truong

(57) ABSTRACT

A therapeutic composition is provided that comprises a 1-R1-phenyl, 4-R2-phenyl substituted 1,2,3,6-tetrahydropyrimidine-2-one sensory nerve receptor agonist in a therapeutically effective amount. The sensory nerve receptor agonist may be represented by the general formula 1-[R1-phenyl]-4-[R2-phenyl]-1,2,3,6-tetrahydropyrimidine-2-one wherein: R1 is -hydroxy, -chloro, -fluoro, -alkyl, -acetoxy, -trifluoromethyl; and R2 is -nitro, -chloro, -fluoro, -alkyl, -trifluoromethyl. Therapeutic compositions of the invention reduce pain, itch, and a sense of discomfort, when formulated for topical delivery to the human lips, mouth, and to the anorectal area.

12 Claims, No Drawings

1,2,3,6-TETRAHYDROPYRIMIDINE-2-ONE COMPOSITIONS AND THERAPEUTIC METHODS THEREWITH FOR PAIN AND INFLAMMATION

CROSS-REFERENCE TO RELATED APPLICATIONS

This application is a continuation-in-part of Ser. No. 10/139193, filed May 2, 2002, inventor Wei, entitled "Therapeutic 1,2,3,6-Tetrahydropyrimidine-2-One Compositions and Methods Therewith", incorporated by reference.

STATEMENT REGARDING FEDERALLY SPONSORED RESEARCH OR DEVELOPMENT

Not applicable.

BACKGROUND OF THE INVENTION

1. Field of the Invention

This invention generally relates to therapeutic compositions formulated for topical delivery to the surfaces of the human lips, mouth, and the anorectal area. This invention more particularly relates to a class of chemicals that activate receptors on sensory nerve endings at or near the entrance and exit of the human gastrointestinal tract and therapeutic use of these chemicals for pain and inflammation. The particularly preferred embodiment compositions are formulated as an ointment, cream, paste, aerosol or suppository and comprise "icilin", a 1,2,3,6-tetrahydropyrimidine-2-one compound.

2. Description of Related Art

Background on Icilin. 1,2,3,6-Tetrahydropyrimidine-2-one compounds were described in U.S. Pat. No. 3,821,221 (inventors C. Podesva and J.M. Do Nascimentoet al, Jun. 28, 1974). These compounds were thought to have depressant and/or stimulant effects on the central nervous system. In 1972, an abstract described a compound in this series called AG-3-5 (1[2-hydroxyphenyl]4-[3-nitrophenyl]-1,2,3,6-tetrahydropyrimidine-2-one). This prototype elicited a syndrome of "wet dog shake behavior" in rats and monkeys accompanied by hyperthermia, hyperactivity and ptosis. Wei (Chemical stimulants of shaking behavior. Journal of Pharmacy and Pharmacology 28: 722–724, 1976) provided the first detailed report of the actions of AG-3-5 in animals and noted that shaking behavior similar to those of a dog when wet could be evoked in various laboratory animals such as the rat, mouse, cat, dog, gerbils, guinea pigs and hamsters.

Subsequently, Wei (Pharmacological aspects of shaking behavior produced by AG-3-5, TRH, and morphine withdrawal. Federation Proceedings 40: 1491–1496, 1981) reported that 0.1 mg of AG-3-5, dissolved in propylene glycol, applied to the dorsum of the tongue elicited prickling sensations of cold and ingestion of 6 mg mixed in orange juice, on one occasion out of three, produced sensations of coolness on the cheeks and on the inner surfaces of the arms and legs. It was hypothesized that AG-3-5 may produce specific activation of receptors for cold, and that stimulation of these receptors accounted for the shaking seen in laboratory animals. In a subsequent publication (E. T. Wei and D. A. Seid. AG-3-5: A chemical producing sensations of cold. Journal of Pharmacy and Pharmacology 35: 110–112, 1983) the effects of AG-3-5 on shaking behavior in the rat were compared to those of menthol and AG-3-5 was shown to be 400 times more potent than menthol on a molar basis on this behavioral endpoint. AG-3-5 was less toxic than menthol, as measured by the oral median lethal dose in rats. AG-3-5 was named icilin because of its cold-producing properties.

Recently, two independent groups simultaneously cloned a biological macromolecule (called a receptor) from trigeminal sensory neurons of the rat. These receptors belong to the transient receptor potential (TRP) family of ion channels and responded to cold temperature and to menthol. Using a sample provided by Wei, McKemy et al. (Identification of a cold receptor reveals a general role for TRP channels in thermosensation. Nature 416: 52–58, 2002) showed that icilin was about 200 times more potent than menthol in eliciting ion channel current changes in the cloned and transfected TRP(M8) receptor. The ion permeability changes elicited in transfected cells were more robust with icilin than those elicited by menthol, and the presence of extracellular calcium was required for activity. Menthol currents did not require extracellular calcium.

The chemical structure of icilin bears little similarity to that of menthol; the former chemical being a pyrimidine-2-one attached to two phenyl rings, and the latter a cyclohexanol derivative. Activation of the TRP(M8) receptor on the neuronal membrane may lead to depolarization of the sensory nerve ending and send action potentials towards the spinal cord and brain that are eventually recognized as psychic signals of skin stimulation.

Background on Pain and Inflammation of the Oral and Anal Areas.

The mouth is the entrance to the gastrointestinal tract and the anus is the exit. At the point of entrance and exit, the surfaces change from thicker skin to thinner skin, and then to mucous membrane. The border between the skin and mucous membrane is called a mucocutaneous junction. The anatomy of the lips illustrates this transition. The lips present three surfaces and a core. The external surface is thin skin with hair follicles, sebaceous glands, and sweat glands. The second surface is the transition zone or vermilion border; it has no hair follicles or sweat glands and is the external border of the lips. The lips have a pinkish red color due to underlying rich blood capillary network and its forms a transition from keratinized to nonkeratinized epithelium. The inner surface of the lips and mouth is nonkeratinized stratified squamous epithelium and the underlying tissue contains numerous small mucous glands and mucoserous salivary (labial) glands. The central core of the lips is composed of striated muscle embedded in elastic fibroconnective tissue.

The perineum is the skin between the anus and the genitalia and has the typical keratinized epithelium of normal skin. The anatomy of the anus is similar in histology to the lips. The anal epithelium (skin) extends about 1.5 cm inside from the anal verge (external edge) and transits from keratinized to nonkeratinized epithelium at the dentate line, the part that demarcates the anus from the rectum. The rectal surface is a mucous membrane and is not keratinized.

The skin epithelia of the lips and anus and surrounding tissues are densely innervated with sensory nerve fibers and these afferent (A delta and C) fibers code for pain and temperature signals. When the lips or anus, or the tissues surrounding, are injured, the subsequent inflammation stimulates the somatosensory nerve endings and the result is pain and sometimes itch. By contrast, the visceral sensory nerve endings that innervate the mucous membrane of the inner lips, mouth, and rectum do not transmit discrete, localized signals of pain, but are sensitive to stretch. Stimulation of rectal nerve endings produces a sense of distension, an urge to have a bowel movement, flatulence, and, if the stimulation is excessive, rectal pain and discomforts.

Inflammatory Conditions of the Lips and Mouth. The skin and mucosa of the lips are demarcated by the vermilion border. The mucosa seen on viewing the face is keratinized and dry; the mucosa of the inner aspect of the lips is nonkeratinized and moist. Branches of the 5th cranial nerve (trigeminal) innervate these tissues. Non-specific disorders can cause inflammation around the mouth and lips. These include immunological disorders, such as pemphigus, pemphigoid, lichen planus; infections, such as venereally transmitted warts (condyloma cuminatum) and herpes simplex; metaplasia, such as dyskeratosis; and physical causes, such as lip and mouth surgery, sunlight, and wind. Some common conditions affecting the surface of the mouth and lips are:

Angular Cheilitis—Chelitis is the technical term for inflammation of the lips. Angular cheilitis occurs at the corners of the lips. This lesion is seen as dry, scaly, red skin and there may be a fissure or slit in the mucocutaneous junction, causing severe pain when the mouth is opened wide. Angular cheilitis may be caused by dry weather, too much sunlight, allergic reactions, or excessive salivation. Cheilitis is also seen more frequently in persons who have reduced immune function, viral infections, or persistent yeast infection. Other forms of inflammation of the lips are cracking exfoliative cheilitis, cheilitis glandularis, and cheilitis granulomatosa.

"Cold sores" or herpes labialis, are the result of an infection with a common virus known as herpes simplex. The sores begin as a group of small red bumps that blister. Itching and burning of the area precedes the prodroma phase (the time for onset of sores). The blisters begin to dry up after a few days and form a yellow crust. The crust then falls off and the redness slowly goes away. The whole process takes about 10 to 14 days. The sores frequently occur on the vermilion border and on the corners of the lips. Infections are more common in immunodeficient individuals, and the blisters themselves are infectious.

"Canker sores" or recurrent apthous ulcers, are inflammatory spots found on the inside linings of the lips and cheeks and in movable parts of the mouth such as the tongue. The small reddish swellings may be painful, especially if they occur in parts of the mouth in contact with the chewing of food. The sores generally heal within 2 weeks. The causes of canker sores are not known, but the incidence of occurrence may be as high as 20 to 25%.

Stomatits, or inflammation of the inner mouth, can occur after infections, or when cancer chemotherapeutic drugs are administered (a condition that is also called mucositis), or when the head and neck are irradiated for cancer treatment.

Inflammatory Conditions of the Anorectal Area. The area between the anus and the genitalia is called the perineum. The anus is the orifice at the terminus of the intestinal tract. Just behind the anus is the anal canal wherein lies the exterior sphincter and the interior sphincter. A sphincter is a circular muscle that constricts and relaxes. Anal sphincters constrict to retain feces and expand to allow it and flatus to pass during defecation. The anal canal is the first 2 inches of skin after the anus; it is closed while at rest and open during defecation. It leads to the rectum, the cavity that runs vertically from the end of the colon to the anal canal. The rectum is approximately 5 inches long and 1.5 inches wide. It stores feces prior to defecation. The term "anorectal area" is defined herein to include the perineum, anus and rectum of a human. More particularly, the term includes the external anus, the internal anus and the lower rectum.

The nerve supply of the anorectal area controls its sensory and motor functions. The inferior rectal nerve, a branch of the pudendal nerve, innervates the lower portion of the anal canal and the external sphincter. These tissues have somatosensory nerve endings, responding to pain, touch and temperature. By contrast, the hypogastric nerve (a visceral nerve because it is part of the autonomic nervous system) innervates the upper portion of the anal canal, internal sphincter and rectum. The sensory nerve endings of the hypogastric nerve respond to distension and transmit visceral afferent signals, including pressure, pain and temperature, to the spinal cord, but discrete sensations are not localized. Instead, over-stimulation of the visceral sensory nerve endings evokes a sense of bloat, distension, cramping, and an urge to defecate.

Many agents or conditions can cause injury to the tissues of the anorectal area and produce pain and inflammation. The primary symptoms are pain and itch but if the inflammation extends to the lower bowel mucosa (rectum, colon, ileum) and its nerve endings, there are also distressing sensations of visceral discomfort. Some of the pathological conditions are described below.

Perineal Dermatitis. Inflammation of perineal skin occurs when urine or feces, because of incontinence, irritates the skin. Pads (e.g. diapers) or other containment devices for incontinence may exacerbate inflammation by causing perspiration and prolonging contact of irritants with tissues. The dermatitis that results causes itch, pain, infections and may lead to ulceration of the skin. Treatment using cleansers, moisturizers, moisture barriers—including ointments, creams, powders, pastes, and lipid barrier films, are discussed by Gray et al. (Perineal Skin Care for the Incontinent Patient. Advances in Skin and Woundcare 15: 170–177, 2002), incorporated herein by reference. An ointment, powder, aerosol or paste containing icilin will alleviate pain and itch of such conditions in the elderly and in the infant (e.g. diaper rash) and facilitate therapeutic management.

Anal Fissure. A fissure is a break or slit in tissue usually at the junction of skin and mucous membrane (mucocutaneous junction). If the fissure occurs on the corner of the mouth, it is called angular cheilitis and opening the mouth can cause pain. An anal fissure is a small tear in the skin of the anus. The fissure can bleed, itch, and become extremely sore during and after defecation, making bowel movements, sitting, and sex painful. Anal sex without lubrication, a hard bowel movement, and inflammation of anal tissue can cause a fissure. Some heal within a couple of weeks, especially if therapeutic cream, warm baths, and stool softeners are used. Others require surgical correction of the tear but this is associated with a subsequent risk of incontinence. Ointments for the treatment of anal fissure have been described in a patent from Cellegy U.S. Pat. No. 6,391,869, incorporated herein by reference. These ointments contain, as active ingredients, substances that release nitric oxide and increase cyclic AMP of smooth muscle cells in the internal anal sphincter. The nitric oxide relaxes the sphincter smooth muscle and the reduced tension decreases pain signals from the fissure.

Hemorrhoids. Hemorrhoids are swollen veins that may protrude outside the anus or reside inside the anal canal. The veins may become inflamed, blocked, or broken and cause fecal contamination of perianal skin. Hence, hemorrhoids may bleed and cause pain and itching because of incontinence and excessive wiping (pruritus ani). Risk factors for hemorrhoids include strenuous or frequent bowel movements that raise intra-abdominal pressure and impede venous return. Related risk factors for developing hemorrhoids are birth trauma and lifting weights.

Sexually Transmitted Diseases. A number of sexually transmitted diseases (STD) can have local effects on tissues in the anorectal region, producing pain, itch, redness and blisters. These STD include:

Herpes simplex virus (HSV) is an infection of the skin and genital mucosa (mucous membrane) causing recurring sores and pain Gonorrhea: inflammation of genital mucosa, causing infectious and painful discharge Human papillomavirus (HPV) causes genital and anal warts Proctitis is inflammation of the lining of the rectum. Proctitis can be short term (acute) or long term (chronic). Proctitis has many causes. It may be a side effect of autoimmune diseases of the lower bowel, such as ulcerative colitis and Crohn's disease. Sexually transmitted diseases may cause proctitis. Proctitis is frequently a side-effect of radiation used to treat prostate cancer or cancer of the female organs. The rectum resides just behind the prostate in the male and the vagina and uterus in the female, so when these organs are irradiated, the bowel wall is injured. Radiation proctitis is manifested as the new growth of many tiny blood vessels on the epithelial surface of the rectum. These blood vessels are fragile and bleed with minimal trauma, resulting in blood in the stool. If the bleeding is severe, anemia or a low red cell blood count can occur. Other causes of proctitis include traumatic rectal injury, allergies, and malfunction of the nerves in the rectum.

Pathogenic organisms that may cause anorectal inflammation are Salmonella, Shigella, Campylobacter, Entamoeba histolytica, Giardia lamblia, *Mycobacterium avium-intracellulare*, Cryptosporidium, Microsporidium, and Cytomegaolvirus. Patients infected with human immunodeficiency virus or receiving immunosuppressive drugs are especially susceptible to infectious agents attacking the lower gut lining and surrounding tissues.

The most common manifestation of proctitis is a frequent or continuous sensation of an urge to have a bowel movement. This distressing but ineffectual urge to empty the rectum is called tenesmus. Other symptoms include constipation, a feeling of rectal fullness, left-sided abdominal pain, passage of mucus through the rectum, rectal bleeding, and anorectal pain. Proctitis because it leads to bleeding, some incontinence, and inflammation will produce subjective discomfort, pain, and itch in the entire anorectal area.

Physicians diagnose proctitis by looking inside the rectum with a proctoscope or a sigmoidoscope. Redness, bleeding, or increased growth of blood vessels are indices of inflammation. A biopsy of tissue from the rectum may confirm the presence of inflammatory cells, diseases, or infections. Treatment depends on the cause of proctitis. For example, the physician may prescribe antibiotics for proctitis caused by bacterial infection. If the inflammation is caused by ulcerative colitis or Crohn's disease, the physician may recommend a drug such 5-aminosalicyclic acid or a glucocorticosteroid. These drugs may be applied directly to the area, as a suppository, or taken orally as a pill. Radiation proctitis may also be treated with analgesics and loperamide, an anti-diarrhea drug with localized actions.

BRIEF SUMMARY OF THE INVENTION

In one embodiment of the present invention, a composition is provided that comprises a 1-R1-phenyl, 4-R2-phenyl substituted 1,2,3,6-tetrahydropyrimidine-2-one sensory nerve endings receptor agonist, preferably formulated as a topical ointment, cream, lotion, lozenge, paste, powder, aerosol, suppository or enema, that is therapeutically effective, such as to relieve pain, when delivered to the lips, mouth, anus and surrounding tissues. The sensory nerve endings receptor agonist may be represented by the general formula 1-[R1-phenyl]-4-[R2-phenyl]-1,2,3,6-tetrahydropyrimidine-2-one wherein: R1 is -hydroxy, -chloro, -fluoro, -alkyl (with about 2 to 4 carbons), -acetoxy, -trifluoromethyl; and R2 is -nitro, -chloro, -fluoro, -alkyl, -trifluoromethyl.

A particularly preferred sensory nerve endings receptor agonist embodiment is called "icilin" and a particularly preferred composition comprises icilin formulated as an ointment, cream or suppository. Icilin formulated and administered as an ointment or cream offers improved therapeutic benefit for the treatment of inflammation of the lips, anorectal area and surrounding tissues. The inventive compositions can also be applied to and/or carried on a suppository, such as for treatment of hemorrhoids, or formulated for administration as an aerosol.

A particularly preferred method of treating cheilitis, perineal inflammation (irritant dermatitis), or anal fissures in a human comprises topically administering a composition comprising 1-[2-hydroxyphenyl]4-[3-nitrophenyl]-1,2,3,6-tetrahydropyrimidine -2-one or an analog, wherein the 1-[2-hydroxyphenyl]-4-[3-nitrophenyl]-1,2,3,6-tetrahydropymidine-2-one or an analog preferably in an amount of at least about 1 to 8% by weight of the composition, more preferably about 3% of the composition.

The further advantages and aspects of the present invention will be understood by reading the following detailed description and the accompanying claims.

DETAILED DESCRIPTION OF THE INVENTION

I have found that icilin and related analogs elicit sensations of cold and anesthetic action when applied topically to the surfaces of the lips and anus, and in surrounding tissues. The effects of cold and numbing are also felt on the inside of the mouth and the tongue; that is, on mucous membranes. These actions can counteract the pain and itch produced in these tissues by inflammation, much like the effects of ice applied to injury.

Uses of Icilin Compounds in Treatment of Inflammation of the Lips, Mouth, and the Anorectal Area. In the parent patent submission, of which this is a continuation-in-part, I described examples whereby topical applications of icilin produced cold sensations on skin and mucous membranes. The somatosensory nerve endings of the lips, mouth, and anorectal area contain receptors that recognize signals coding for pressure, cold and heat/pain. The receptors are coupled to specific cation channels on the nerve membrane and these receptors, when stimulated, cause afferent neuronal transmission to the spinal cord and brain. The specific cold receptor is called TRP(M8) receptor and has a unique molecular composition. The specific receptor for heat/pain has another configuration and is called the vanilloid receptor.

It is recognized for a long time that ice has anti-inflammatory properties and reduces pain (analgesia). Topical application of ice has been used for reducing the discomfort of cold sores on the lips and for the pain of anal fissures, but repeated applications of ice are inconvenient for these conditions. While it is tempting to attribute the actions of ice solely to stimulation of the TRP(M8) receptor, this conclusion is not warranted because: a) ice also causes constriction of blood vessels, b) ice reduces the metabolic activity of cells and may inhibit the release of inflammatory substances (mediators) and c) ice may affect activity of other receptors, as well as affect the process of neurotransmission itself, and the like. Thus, the effects of ice on sensory perception and on inflammation are an empirical observation.

Icilin and related analogs, applied locally as an ointment or cream, or delivered via a suppository or aerosol, produce sensations of cold and reduces the sensations of pain and irritation. These actions attenuate the symptomatic discomforts of cheilitis, stomatitis, mucositis, proctitis and perineal inflammation. The sensory effects of icilin compounds are the basis and mechanisms for its use in treatment of pain, itch and inflammation of the skin, lips; mucous lining of the mouth and anorectal area Without being bound by theory, I hypothesize that the target of icilin actions may be the TRP(M8) receptor, but suspect that at the molecular level other receptors are being affected as well. The observations of the beneficial actions of icilin and related compounds are empirical findings.

The word "agonist" was introduced by Reuse ("Comparisons of various histamine antagonists. British Journal of Pharmacology vol.3, pgs. 174–180, 1948) to denote a chemical that activates biological events. A sensory nerve ending is the part of the nerve that, when activated, initiates events that convey signals to the spinal cord and brain. These signals may be translated to sensory experience. Thus, a sensory nerve ending receptor agonist is a chemical that acts on targets on the sensory nerve ending to produce changes in sensation.

Delivery of Icilin Compounds to Targets. Compositions and therapeutic methods in accordance with this invention utilize a 1-R1-phenyl, 4-R2-phenyl substituted 1,2,3,6-tetrahydropyrimidine-2-one sensory nerve endings receptor agonist, preferably of the general formula 1-[R1-phenyl]-4-[R2-phenyl]-1,2,3,6-tetrahydropyrimidine-2-one wherein: R1 preferably is -hydroxy, -chloro, -fluoro, -alkyl (with about 2 to about 4 carbon atoms)-acetoxy, -trifluoromethyl; and R2 preferably is -nitro, -chloro, -fluoro, -alkyl (with about 2 to 4 carbons), -trifluoromethyl. I refer to the particularly preferred compound and its analogs as "icilin" and its analogs as "icilin analogs". Formula 1 illustrates the general formula and icilin is represented by Formula 2.

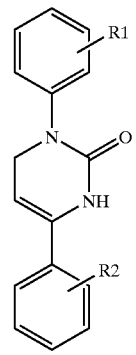

Formula 1: 1-R1-phenyl, R2-phenyl, substituted 1,2,3,6-tetrahydropyrimidine-2-one.

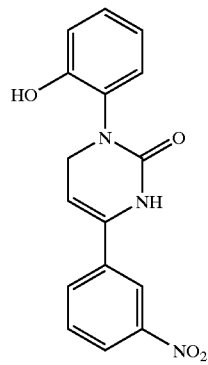

Formula 2: Icilin, 1-[2-hydroxy]-4-[3-nitrophenyl]-1,2,3,6-tetrahydropyridimine-2-one.

Icilin is a lemon yellow crystalline powder with a molecular weight of 311 Daltons and a melting point of 229 to 231° C. The powder is without odor and non-irritating, meaning that it does not elicit any smell or unpleasant sensations upon contact with the surfaces of the human body. The compound is stable at room temperature. Icilin is readily soluble in organic solvents such as dimethylsulfoxide, nitromethane, dimethylacetamide and, after warming, in propanediols; slightly soluble in ethanol and acetone; and virtually insoluble in water. Thus, icilin would be considered as a lipophilic, hydrophobic compound that is not easily miscible with aqueous systems. Analogs of icilin, for example, with acetyoxy, ethyl, fluoro, or trifluoromethyl substitutions, retain similar chemical and physical properties and are included within the scope of this invention.

Methods suitable for the preparation of the Formula 1 and Formula 2 compounds are described by Podesva and Do Nascimento, U.S. Pat. No. 3,821,221, issued Jun. 28, 1974, incorporated herein by reference, and are exemplified by Example A hereinafter. Further, the examples 1–6 show the effects of topical application of icilin on skin and mucous membranes to relieve pain of angular cheilitis and pain and itch of hemorrhoidal discomfort. Icilin, administered via a suppository or as an enema, reduces anorectal pain.

Formulation of Icilin Compounds for Topical Delivery to Targets. Pharmaceutical carriers or vehicles suitable for the topical administration of icilin and combinations provided herein to the lips, mouth, or anorectal area include any such carriers known to those skilled in the art to be suitable for the particular mode of administration. The effective concentration may be determined empirically by testing the compounds using in vitro and in vivo systems. Thus, methods for preparing solutions, emulsions and suspensions, using standard methods for formulated Medical Topicals are well known to the art (J. G. Nair, Chapt. 39: Solutions, Emulsions, Suspensions and Extracts, pg. 721–752 and L. H. Block, Chapt. 44, Medicated Topicals, pg. 836–857, in "Remington, the science and practice of pharmacy," Alfonso R. Gennaro, Chairman of the editorial board and editor. 20th ed. Baltimore, Md.: Lippincott Williams & Wilkins, 2000). The recipes for ointment preparation are also on the Internet (www.pharmlabs.unc.edu) site of the School of Pharmacy, University of North Carolina, Chapel Hill. The selected icilin compound of this invention may be dispersed in various vehicles as an emulsion wherein it is either in a suspension or is solubilized, and is in either the aqueous or the oil phase.

The rate of drug absorption across the skin surface is dependent on drug concentration in the formulation, its solubility and its oil/water partition co-efficient. The physical form of icilin to be delivered to the receptors of the sensory nerve endings is optimized by design for penetration of barriers, receptor activation, and sufficient duration of action. Although icilin may be administered as a solution, for example dissolved in a solvent such as propylene glycol, it is more preferably suspended in this solvent as a solid and admixed as an emulsion in an ointment or cream. Before formulation, icilin may be milled to a fine particle size, modified by recrystallization to a particle with maximal surface area, incorporated onto nanospheres, or incorporated into nanoparticles or liposomes, to maximize biological activity and duration of action using such methods as are now known in the art.

Compositions of the present invention with icilin and/or icilin analogs may be formulated as liniments (defined as a preparation that may be liquid or semiliquid intended for external application) or more preferably as ointments or creams. Standard ointment formulations may be used for delivery to the lips and anorectal surfaces. Thus, particularly preferred embodiments of this invention are wherein icilin is used in a non-irritating ointment, cream or lotion. In Example A, I describe a 2% solution of icilin formulated in an Aquaphor® ointment and used it for investigation. The ingredients in the commercially available Aquaphor® ointment are petrolatum, mineral oil, ceresin, lanolin alcohol, pathenol, glycerin and bisabolol. This product is quite similar in consistency to pure petrolatum (Vaseline®), but somewhat less viscous, and is non-irritating. The details for preparation of the ointment are given in Example A. It is to be understood that the concentration ranges set forth herein are exemplary only and are not intended to limit the scope or practice of the claimed formulations.

The Formula I compounds are typically included at concentration of 0.1% w/w up to 20% w/w. Preferable concentrations are in the range of 0.5% w/w to about 20% w/w, more preferably 1% w/w to 20% w/w, yet more preferably greater than about 1% w/w to about 10% w/w, and most preferably greater than 1% w/w up to about 5% w/w. Aqueous suspensions and formulations contain 1% w/w or more.

The U.S. Pharmacopoeia recognizes four general classes of ointment bases. The formulation in Example A is in the category of "Absorption Bases (Anhydrous)". Another ointment in the "Absorption Bases (water in oil type)" would be composed of icilin, 1.0 to 8% by weight, and containing emulsifying wax, white petrolatum, purified water and propylene glycol, butylated hydroxyanisole, propyl gallate, citric acid and lactic acid. Other ingredients in a topical ointment formulation may include lanolin, paraffin wax, vegetable oils, such as peanut or castor oil, aloe vera, and sorbital sequioleate. A lotion containing icilin, 0.3 to 2% by weight, may be composed of a smooth, homogeneous, opaque emulsion composed of benzyl alcohol 2% (wt/wt) as preservative, emulsifyng wax, glycerin, isopropyl palmitate, lactic acid, purified water, and polyethylene glycol 400. A more viscous ointment may contain these ingredients: a homogeneous melt of 50% methyl salicylate, 25% white beeswax, 25% anhydrous lanolin to which is added 3% by weight of icilin. The mixture is warmed and then allowed to solidify. A soft ointment results having a soothing effect on the anorectal area. Further, icilin may also be formulated in Hydrophilic Petrolatum USP, using 30 g cholesterol, 30 g stearyl alcohol, 80 g white wax, 860 g white petrolatum, combined with 20 g icilin in 110 ml propylene glycol.

There are standard procedures for the actual mixing and preparing ointments with petrolatum or oleaginous bases. The finely powdered icilin is levigated thoroughly with a small quantity of the base to form a concentrate. The concentrate then is diluted geometrically with the remainder of the base to form a uniformly dispersed ointment in a petrolatum or oleaginous base.

The solvent used for wetting, suspending or dissolving icilin may be a nonaqueous pharmacologically approved solvent with non-irritating properties. Suitable organic materials useful as the solvent or a part of a carrier system are as follows: propylene glycol, polyethylene glycol (M.W. 200–600), polypropylene glycol (M.W. 425–2025), glycerine, sorbitol esters, butanediol and mixtures thereof. Other examples include ethoxydiglycol, and 1-methyl-2-pyrrolidone, purified water, saline solution, polyethylene glycol, glycerine, glycerine polymethacrylate, white ointment, petroleum jelly (petrolatum), lanolin, beeswax, cholesterol alone or in combination. The preferred vehicle for levigation use in this invention is a propanediol, containing in the finished product 1 to 8% of Formula 1 compounds by weight. In certain situations, aqueous suspensions, gels, pastes, foams, aerosols, and sprays may also be considered for topical administration.

For longer term application of icilin to the anorectal area or for the inner lining of the mouth, a suppository or a paste may be used. Thus, for example, icilin may be incorporated into a mucoadhesive polymer such as polyvinylpyrrolidone, polycarbophil or sodium alginate, for use as a suppository. The suppository may be applied as a liquid at room temperature, which then gels in the anorectal surface at body temperature and adheres to the mucous membrane. Other examples of formulations for delivery of drugs to the anorectal area are described in U.S. Pat. No. 6,391,869, incorporated herein by reference.

For mucoadhesive pastes to be applied to the lining of the mouth or to the gums, one may use Orabase®. Chemically Orabase® consists of plasticized hydrocarbongel, guar gum, carboxymethylcellulose, tragacanth gum and pectin. Orabase® is an adhesive-vehicle preparation and was designed for the purpose of retaining topically applied drugs on the oral mucous membranes. Studies with this preparation indicate that it adheres to the oral mucosa for 2 hours or longer, the duration being dependent on the degree of mobility of the oral tissues, the washing action of saliva and the amount of vehicle applied. Other oral mucoadhesive compounds are described in U.S. Pat. No. 6,319,513.

For certain inflamed body parts, such as the lining of the mouth and the surfaces of wounds on the skin, the preferred delivery mechanism may be the use of an aerosol. An aerosol has been defined as a colloidal system consisting of very finely divided liquid or solid particles dispersed in or surrounded by a gas. Thus, a gas, typically air, is used to deliver icilin compounds in solution or as solid particles to biological targets in skin or mucous membranes.

An aerosol dosage form has the advantages of: a) ease of use, for example, the absence of need of cotton swab or other applicators, b) simple dose titration to individual needs, for example, when used for pain from mucositis in the mouth, c) no danger of contamination of the medication, as the unused portion is sealed in the package, d) rapid onset of action, for example, if the drug is formulated in solution, and e) reasonable control of dosage by selecting the proper nozzle valve and container. The aerosol may be used to deliver icilin compounds and compositions as a spray, foam or semi-solid. Methods for aerosol delivery and formulations are described by Sciarra et al., Chpt. 50, "Aerosols" in "Remington, the science and practice of pharmacy," Alfonso R. Gennaro, Chairman of the editorial board and editor. 20th ed. Baltimore, Md. Lippincott Williams & Wilkins, 2000, incorporated here by reference.

For the icilin compounds, specialized propellant gases are typically not required for delivery of drug to skin and mucous membrane surfaces, and a simple manual air pump is likely to suffice. Such dispensers, used for buccal and nasal spray delivery, are well known to the art and available commercially. For example, Nature Well uses a 10-ml spray bottle to deliver Migra Spray® to the buccal mucosa, using digital pressure for generating the airflow.

For icilin compounds and compositions applied to mucous membranes such as the oral cavity or the anogenital region, a preferred formulation is an emulsion with oil/water foam characteristics, similar to quick-breaking shaving foam. This avoids a "wet" dripping solution applied to the skin surface. Such a formulation may be achieved by dissolving icilin compounds in propylene glycol, then adding additional substituted glycols and glycol derivatives, then adding glycerin and purified water and appropriate preservatives. A thickener may be added if the spray is used to deliver drug to skin ulcers or wounds, such as, for example, occurs after traumatic injury, burns, or ulcers from pressure or endocrine disorders (e.g. diabetic skin ulcers). For delivery into the oral cavity, however, a water/oil formulation, that is, a formulation with a higher percentage of water, would preferably deliver aerosol foam more rapidly to the target.

The concentrations of icilin compound in aerosol preferably range from 1% to 20% depending on the severity of the pain or itch condition that is being experienced. For example, for sunburns of the lips and face, a concentration of about 2 to 4% icilin emulsion/foam may be sufficient for rapid pain relief. On the other hand, when used for relieving the pain of wound debridement in a bun patient or for treating a soldier who has been wounded in a blast injury and recovering from surgery, a 10% icilin emulsion/foam would provide more long-lasting relief.

Compositions of the present invention with icilin and/or icilin analogs for the lips and anus may preferably further comprise a single pharmaceutical or a combination of pharmaceuticals (wherein the pharmaceutical has some desired biological activity). The use of an icilin product in combination with one or more pharmaceutical agents is particularly useful to facilitate therapy of the lips or anorectal disorder.

Thus, an antifungal agent may be used for yeast infections of the lips or anus. An anti-viral agent, such as acyclovir or docosanol, maybe combined with icilin for treatment of cold sores on the lips. A smooth muscle relaxant such as minoxidil may be combined with icilin for the treatment of anal fissures. A gel containing a growth factor (Regranex®) may be formulated with icilin to treat skin ulcers or anal fistulae.

Additional pharmaceuticals that may be used in combination with icilin include anti-inflammatory analgesic agents, anti-inflammatory steroidal agents, antihistamines, sympathomimetic amine vasoconstrictors, smooth muscle relaxants, menthol and menthol analogs, local anesthetics, antibiotics and keratolytics.

Examples of anti-inflammatory analgesic agents include methyl salicylate, monoglycol salicylate, aspirin, indomethacin, diclofenac, ibuprofen, ketoprofen, naproxen, pranoprofen, fenoprofen, sulindac, fenclofenac, clidanac, flurbiprofen, fentiazac, bufexamac, piroxicarn, pentazocine, etc.

Examples of steroidal anti-inflammatory agents include hydrocortisone, prednisolone, dexamethasone, triamcinolone acetonide, fluocinolone acetonide, hydrocortisone acetate, prednisolone acetate, methylprednisolone, dexamethasone acetate, betamethasone, betamethasone valerate, flumetasone, fluticasone, budesonide, fluorometholone, beclomethasone dipproprionate, etc.

Examples of antihistamines include diphenhydramine hydrochloride, diphenhydramine salicylate, diphenhydramine, chlorpheniramine maleate, promethazine hydrochloride, etc.

Examples of sympathomimetic amine vasoconstrictors include phenylephrine hydrochloride and oxymetazoline.

Examples of local anesthetics include dibucaine hydrochloride, dibucaine, lidocaine hydrochloride, lidocaine, benzocaine, pramoxine hydrochloride, tetracaine, tetracaine hydrochloride, oxyprocaine hydrochloride, mepivacaine, and piperocaine hydrochloride.

Examples of smooth muscle relaxants include nitric oxide donors, such as minoxidil, isorbide dinitate, and phosphodiesterase inhibitors, such as aminophylline. Other examples of smooth muscle relaxants that may be given in combination with icilin to achieve relaxation of the internal anal sphincter in anal fissures are described in U.S. Pat. No. 6,391,869.

Examples of antibiotics include neomycin and the antiviral agent docosanol (Abreva®), and examples of keratolytics include such agents as, alpha-hydroxy acids, glycolic acid and salicylic acid.

Examples of menthol analogs include WS-3 and WS-23, both menthol analogs having Generally Recognized As Safe status by regulatory authorities; WS-158 and other phosphine oxide menthol analogs; menthone glycerol ketal, menthyl lactate, menthoxypropane-1,2-diol and cyclic alpha-keto enamines such as 4-methyl-3-(1-pyrrolidinyl)-2-[5H]-furanone.

Other drugs that may be used in combination are Protopic® tacrolimus) and Elidel® (pimecrolimus), both of which are topical immunosuppressive drugs used in the treatment of dermatitis.

Without limiting the present invention, a number of examples are now described. In the below experimental section, Example A describes a preparation and formulation of icilin and analogs, while Examples 1–6 describe therapeutic uses of the invention with human subjects.

EXPERIMENTAL

Example A

Chemical Synthesis of Icilin and Analogs. The methods of chemical synthesis are as described by Podesva and Do Nascimento U.S. Pat. No. 3,821,221, incorporated by reference. Briefly, a substituted acetophenone, e.g. 3-nitroacetophenone or 3-trifuoromethylacetophenone, readily obtainable from commercial sources such as Sigma-Aldrich, Co., is mixed with diethylamine or dimethylamine in formaldehyde and refluxed in acidic solutions. After addition of a second substituent (e.g. ortho-aminophenol), the Mannich reaction produces a β-amino-ketone compound ([β-ortho-hydroxyanilino]-meta-nitropropiophenone) which is isolated. This reagent is then reacted with potassium cyanate or sodium cyanate to produce an unstable urea intermediate that proceeds to cyclize into the tetrahydropyrimidine-2-one ring, with the appropriate groups on position 1 (2-hydroxyphenyl) and 4 (3-nitrophenyl) on the 1,2,3,6-tetrahydropyrimidine-2-one ring. The precipitated product is readily collected by filtration and may be recrystallized using solvents such ethyl acetate or purified on silica gel columns. The final products are solids stable at room temperature.

A 2% icilin ointment was prepared by adding 10 grams of icilin (in powder form) to 100 ml of propylene glycol (1,2-propanediol) at room temperature. The propylene glycol was used as "wetting (levigating) agent" to suspend the icilin in an uniform liquid medium. This liquid icilin suspension was then progressively admixed in batches with 400 grams of commercial Aquaphor® ointment (produced by Beiersdort Inc. a German Company with U.S. offices in Wilton, Conn.) to obtain the test ointment, which was stored in standard 1 oz. vials. This ointment was prepared by the Drug Product Services Laboratory of the University of California, San Francisco, under the direction of an experienced Ph.D., Pharm. D. investigator.

Example 1

A male subject had angular cheilitis that was due to seasonal allergies and dry weather. Pain was experienced upon opening the mouth to a wider angle, such as in brushing of the teeth, and in the use of dental floss to clean molars. The subject used a cotton-tipped swab stick to apply 0.3 to 0.5 cc of the 2% icilin ointment prepared as in Example A to the corners of his mouth and to the vermilion borders. Within several minutes, cooling and soothing were felt in the lip region and the pain at the corners of the mouth was attenuated. There were also punctate discharges of cold spots and the effects were felt as "sparkling". In an additional experiment, three normal subjects were tested and these effects of icilin ointment on the lip region were readily demonstrated and experienced.

Example 2

A 65-year old male subject had recurrent episodes of cold sores. With the onset of a respiratory ailment, due probably to excess alcohol consumption and cigar smoking, he anticipated the development of cold sores. The subject used a cotton-tipped swab stick to apply 0.2 to 0.4 cc of the 2% icilin ointment to the upper portion on his lips during the "prodroma" phase of the infection and reported that itchiness was diminished. Nevertheless, after two days, red papules and small blisters appeared on the upper vermilion border with characteristic pain and itch. Application of 2% icilin ointment to the lips resulted, within two to three minutes, in tingling and cooling sensations on the lips, followed by numbness, with subjective relief of discomfort. The subject repeated icilin applications with similar relief, until the cold sores disappeared 10 days after onset.

Example 3

A male subject used a swab-stick to applied 3 mg of powdered icilin onto his buccal mucosa Sensations of cold were felt inside the mouth at the site of application and in adjacent tissues. The effect lasted for about 30 min. An icilin solution was then prepared using 4% icilin dissolved in propylene glycol and mixed 1:1 with sterile water to yield a 2% concentration. The solution was placed in an empty 10 ml bottle with a digital plunger and nozzle valve (Migra Spray® bottle). The aerosol spray of icilin, when applied several times into the mouth, produced the same characteristic sensations of cold and decreased sensitivity. These experiments illustrate that sensory receptors are present within the inner lining of the mouth, and that the contemplated use of icilin in the treatment of stomatitis and canker sores is supported.

Example 4

An adult male subject had periodic bouts of severe skin inflammation in the groin and perineal areas. The causes may have been allergic reactions to laundry detergents or to adhesives used in underwear elastic. Each episode of inflammation was accompanied by red discoloration of the skin and intense itching. The subject applied 0.5 to 0.8 cc of the 2% icilin ointment prepared as in Example A to his inflamed skin and reported that the itch immediately ceased. He also noticed that the discoloration decreased and there has been no recurrence in the last month. The subject expressed satisfaction with use of the ointment.

Example 5

A male subject with inflamed hemorrhoids applied the 2% icilin ointment (prepared as described in Example A in the Aquaphor® ointment) to his anorectal area. The estimated volume of the ointment was about 0.3 to 0.5 cc. Cooling sensations were felt within 5 minutes after application, with the effects extending to the scrotum. Relief of pain and itch in the anorectal area lasted for longer than 2 to 3 hours. In a similar experiment, the 2% icilin ointment was coated onto a commercial suppository, shaped as a 1.5-inch bullet, containing 25 mg of hydrocortisone. The estimated amount of the ointment deposited on the suppository was about 0.3 to 0.6 cc. The suppository was inserted into the anorectal area. Again, cooling sensations with relief of pain, itch and discomfort were obtained, lasting for 2 to 3 hours. In six normal individuals without hemorrhoidal disorders, application of 0.3 to 0.6 cc of the 2% icilin ointment reliably produced cooling and soothing sensations of the anorectal area that lasted for at least two hours.

Example 6

An adult male subject with rectal pain associated with bowel movements, and due to an acute anal fissure, used a cotton-tipped swab stick to apply 0.5 to 0.8 cc of the 2% icilin ointment to his anorectal area and then proceeded immediately to the commode. The pain that normally was associated with defecation was diminished and the subject expressed relief and satisfaction with use of the ointment.

These experiments illustrate that topical application of icilin to human lips, mouth, and the skin and mucous membranes of the anorectal region is non-irritating and elicits cooling and anesthetic sensations that provide symptomatic relief of cheilitis and inflammation of the anorectal area, I conclude that local, topical application of 1,2,3,6-tetrahydropyrimidine-2-one derivatives in a suitable vehicle to these mucocutaneous junctures and nearby tissues relieves pain, itch and discomfort; hence these pharmaceutical formulations are useful in the treatment of inflammatory disorders of these parts of the body.

In summary, I believe that no investigations of icilin on human lips, mouth, and anorectal area have been reported in the scientific literature other than what is discussed or described here. I point out the unique properties of icilin and describe novel compositions and preferred embodiments for therapeutic methods of use.

It is to be understood that while the invention has been described above in conjunction with preferred specific embodiments, the description and examples are intended to illustrate and not limit the scope of the invention, which is defined by the scope of the appended claims.

It is claimed:

1. A composition, useful for the treatment of inflammatory disorders of the lips, mouth, and the anorectal area, comprising:
   a therapeutically effective amount of a sensory nerve endings receptor agonist having the formula 1-[R1-phenyl]-4-[R2-phenyl]-1,2,3,6-tetrahydropyrimidine-2-one, wherein R1 is hydroxy, chloro, fluoro, an alkyl of about 2 to about 4 carbon atoms, acetoxy, or trifluoromethyl
   one or more of an agent selected from the group consisting of an antifungal, an antiviral, a smooth muscle relaxant, an immunosuppressive agent, and a tissue growth factor; and,
   a dermatologically acceptable vehicle in which the sensory nerve endings receptor agonist and the agent are carried.

2. The composition as in claim 1 wherein the sensory nerve endings receptor agonist is in an amount of from about 0.1% w/w to about 15% w/w.

3. The composition as in claim 1 wherein the vehicle includes an oleaginous base.

4. The composition as in claim 1 wherein the vehicle includes an aerosol.

5. The composition as in claim 1 wherein the sensory nerve endings receptor agonist includes 1-[2-hydroxyphenyl]-4-[3-nitrophenyl]-1,2,3,6-tetrahydropyridimine-2-one.

6. A method of relieving pain or itch in treating inflammatory disorders of the lips, mouth and the anorectal area in a human patient, comprising:

topically administering a therapeutically effective amount of the composition of claim 1, wherein a sensory nerve endings receptor agonist having the formula 1-[R1-phenyl]-4-[R2-phenyl]-1,2,3,6-tetrahydropyrimidine-2-one, wherein R1 is hydroxy, chloro, fluoro, an alkyl of about 2 to about 4 carbon atoms, acetoxy, or trifluoromethyl and R2 is nitro, chloro, fluoro, an alkyl of about 2 to 4 carbon atoms or trifluoromethyl, to the lips, mouth or an anorectal area of the patient.

7. The method as in claim 6 wherein the amount of the sensory nerve receptor agonist administered is in an amount of from about 5 mg to about 50 mg per application.

8. The composition as in claim 5 wherein the sensory nerve endings receptor agonist is in an amount of about 1 wt. % to about 10 wt. % of the composition.

9. The composition as in claim 5 wherein the vehicle includes a mucoadhesive polymer, mucoadhesive paste or an aerosol.

10. The method as in claim 6 wherein the sensory nerve endings receptor agonist includes 1-[2-hydroxyphenyl]-4-[3-nitrophenyl]-1,2,3,6-tetrahydropyrimidine-2-one.

11. The method as in claim 10 wherein the sensory nerve endings receptor agonist is carried in a mucoadhesive polymer or paste.

12. The method as in claim 11 wherein the sensory nerve endings receptor agonist is in an amount of greater than about 1 wt. % of the composition.

* * * * *

UNITED STATES PATENT AND TRADEMARK OFFICE
CERTIFICATE OF CORRECTION

PATENT NO. : 6,743,801 B2
DATED : June 1, 2004
INVENTOR(S) : Edward T. Wei

It is certified that error appears in the above-identified patent and that said Letters Patent is hereby corrected as shown below:

Column 14,
Line 55, insert the following:

-- Claim 1. A composition, useful for the treatment of inflammatory disorders of the lips, mouth, and the anorectal area, comprising:
a therapeutically effective amount of a sensory nerve endings receptor agonist having the formula 1-[R1-phenyl]-4-[R2-phenyl]-1,2,3,6-tetrahydropyrimidine-2-one, wherein R1 is hydroxy, chloro, fluoro, an alkyl of about 2 to about 4 carbon atoms, acetoxy, or trifluoromethyl and R2 is nitro, chloro, fluoro, an alkyl or about 2 to 4 carbon atoms or trifluoromethyl;
one or more of an agent selected from the group consisting of an antifungal, an antiviral, a smooth muscle relaxant, an immunosuppressive agent, and a tissue growth factor; and,
a dermatologically acceptable vehicle in which the sensory nerve endings receptor agonist and the agent are carried. --

Signed and Sealed this

Third Day of May, 2005

JON W. DUDAS
*Director of the United States Patent and Trademark Office*